(12) United States Patent
Koike et al.

(10) Patent No.: US 8,132,470 B2
(45) Date of Patent: *Mar. 13, 2012

(54) FLUID FLOW DETECTOR HAVING A MOBILE BODY MOVING BETWEEN A DETECTION CHANNEL AND A DISCHARGE CHANNEL

(75) Inventors: Kazuhiro Koike, Shizuoka-ken (JP); Nobuaki Suzuki, Shizuoka-ken (JP); Motonori Watanabe, Shizuoka-ken (JP); Masatoshi Yokoyama, Shizuoka-ken (JP); Yoshimi Akaike, Shizuoka-ken (JP)

(73) Assignee: Tyco Healthcare Group LP, Mansfield, MA (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/691,787

(22) Filed: Jan. 22, 2010

(65) Prior Publication Data
US 2010/0263455 A1    Oct. 21, 2010

Related U.S. Application Data

(63) Continuation-in-part of application No. 12/542,020, filed on Aug. 17, 2009, now Pat. No. 8,061,218.

(30) Foreign Application Priority Data

Apr. 21, 2009  (JP) ................. 2009-102938

(51) Int. Cl.
*G01F 1/22*  (2006.01)
*A61M 5/00*  (2006.01)

(52) U.S. Cl. .............. 73/861.57; 604/246; 73/861.52

(58) Field of Classification Search ............. None
See application file for complete search history.

(56) References Cited

U.S. PATENT DOCUMENTS

| | | | | |
|---|---|---|---|---|
| 3,416,371 A | * | 12/1968 | Locke | ............. 73/861.57 |
| 4,486,744 A | | 12/1984 | Pratt et al. | |
| 4,699,617 A | * | 10/1987 | Moriuchi et al. | ............. 604/246 |
| 5,019,678 A | * | 5/1991 | Templeton et al. | ..... 200/81.9 M |
| 5,445,622 A | | 8/1995 | Brown | |
| 5,462,525 A | | 10/1995 | Srisathapat et al. | |
| 5,820,715 A | * | 10/1998 | Singleterry et al. | ........ 156/73.1 |
| 6,915,706 B2 | | 7/2005 | Rousselin | |
| 6,935,190 B1 | | 8/2005 | Height et al. | |

OTHER PUBLICATIONS

European Search Report corresponding to European Application No. EP 09 01 0487, completed Dec. 28, 2009; mailed Jan. 7, 2010; 4 pages.

* cited by examiner

*Primary Examiner* — Harshad Patel
(74) *Attorney, Agent, or Firm* — Lisa E. Winsor, Esq.

(57) ABSTRACT

A fluid flow detector includes a detector main body defining a fluid flow channel having a fluid flow detection channel positioned adjacent an upstream hole and a discharge channel positioned adjacent a downstream hole. A mobile body is positioned within the fluid flow channel and dimensioned to be movable along the fluid flow channel. The diameter of the fluid flow detection channel is smaller than the diameter of the discharge channel, and the maximum diameter of the outer peripheral edge part of the face of the fluid flow channel orthogonal to the direction of movement of the mobile body is slightly smaller than the diameter of the fluid flow detection channel. The upstream hole and the downstream hole are formed with a size and shape such that fluid can flow through the upstream and downstream holes without being obstructed by the mobile body.

14 Claims, 5 Drawing Sheets

FLUID FLOW DETECTOR HAVING A MOBILE BODY MOVING BETWEEN A DETECTION CHANNEL AND A DISCHARGE CHANNEL

CROSS REFERENCE TO RELATED APPLICATIONS

This patent application is a continuation-in-part of U.S. patent application Ser. No. 12/542,020, filed on Aug. 17, 2009, the entire contents of which are incorporated herein by this reference.

BACKGROUND

1. Technical Field

The present disclosure relates to a fluid flow apparatus for detecting the flow of a fluid in a transfusion line.

2. Background of Related Art

Fluids such as drug solutions are conventionally supplied to patients using a transfusion line provided with a tube. In such cases, it is difficult to visually confirm the flow of the fluid if there is a small amount of fluid to be administered to the patient. Furthermore, even if a fluid flow detector for detecting the flow of fluid is incorporated into the transfusion line, this fluid flow detector must be such that it does not obstruct administration of the fluid to the patient. In addition, there may be cases where the fluid flow detector is used only once, and an inexpensive fluid flow detector which does not utilize a device such as an electrical sensor or an optical sensor is required in such cases. There are instruments such as this in which a spherical body which moves along with the flow of fluid is provided in the fluid flow detector.

For example, in U.S. Pat. No. 6,915,706, the fluid flow detector (flowmeter) has a configuration in which an upstream port extending horizontally and a conical upper flow channel extending vertically are connected by a narrow passage, and a spherical body is arranged inside the upper flow channel. The upper flow channel is formed so that the upper part has a somewhat larger diameter than the lower part, and the flow of the fluid can be detected by the position of the spherical body which moves inside the upper flow channel depending on the flow of fluid, which also allows the flow rate of the fluid to be measured.

However, with the conventional fluid flow detector described above, it is difficult to detect the flow of fluid if the fluid to be administered to the patient is in an extremely small amount, for example if the flow velocity is of the order of 1 ml per hour. As such, an inexpensive fluid flow detector which can detect the flow of a minute amount of fluid, and a transfusion line provided with same would be desirous.

SUMMARY

Accordingly, a fluid flow detector for detecting the flow of a fluid in a transfusion line includes a detector main body and a mobile body. The detector main body defines a fluid flow channel having a circular cross section and includes an upstream hole formed at an upstream end of the detector main body, a downstream hole formed at a downstream end of the detector main body, a fluid flow detection channel positioned adjacent the upstream hole, and a discharge channel positioned adjacent the downstream hole. The upstream hole and the downstream hole are formed with a size and shape such that fluid can flow through the upstream and the downstream holes without being obstructed by the mobile body, but the mobile body will not pass through them.

The outer peripheral edge part of the face of the fluid flow channel orthogonal to the direction of movement is formed to be circular. The diameter of the fluid flow detection channel is smaller than the diameter of the discharge channel, and the maximum diameter of the outer peripheral edge part of the face of the fluid flow channel orthogonal to the direction of movement of the mobile body is slightly smaller than the diameter of the fluid flow detection channel. An intermediate flow channel is provided between the fluid flow detection channel and the discharge channel. The intermediate flow channel has a diameter that becomes steadily greater from the fluid flow detection channel towards the discharge channel. An inflow pipe comprising a female luer which links in communication with the fluid flow channel is joined to the upstream hole of the detector main body, and an outflow pipe comprising a male luer which links in communication with the fluid flow channel is joined to the downstream hole of the detector main body.

The mobile body is positioned within the fluid flow channel and is dimensioned to be movable along with the fluid flow channel in response to the flow of a fluid inside the fluid flow channel. The mobile body may be a spherical body.

In embodiments, the fluid flow channel includes an upstream hole and a downstream hole that consists of a shape in which the peripheral edge part of the upstream hole and the downstream hole orthogonal to the flow of fluid is elliptical. In embodiments, the fluid flow detector is incorporated into a transfusion line that includes a fluid supply part and a fluid supply channel through which passes a fluid supplied from the fluid supply part, and the fluid flow detector is arranged in the fluid supply channel.

In embodiments, one or more combined detection and discharge channels are positioned between the fluid flow detection channel and the discharge channel. In embodiments, an intermediate flow channel is provided between the fluid flow detection channel, the discharge channel, and the one or more combined detection and discharge channels wherein the intermediate flow channel has a diameter that becomes steadily greater from the fluid flow detection channel towards the discharge channel.

In accordance with one aspect of the present disclosure, a fluid flow detector includes a detector main body defining a fluid flow channel having an upstream end and a downstream end. The fluid flow channel can be dimensioned to accommodate a predetermined minimum flow rate of between about 0.1 ml/hr and about 20 ml/hr. The fluid flow channel defines a fluid flow detection channel disposed on the upstream end and a discharge channel disposed on the downstream end. The discharge channel has a diameter larger than the fluid flow detection channel. One or both of the fluid flow detection and discharge channels of the fluid flow channel may be configured to be visually perceptible to a user.

A mobile body is movably disposed within the fluid flow channel between the fluid flow detection and discharge channels. The diameter of the fluid flow detection channel is slightly larger than the diameter of the mobile body so that fluids may flow past the mobile body within the fluid flow detection channel. The mobile body is configured to be selectively positioned within the fluid flow detection channel to provide indicia of fluid flow within the fluid flow detection channel. The mobile body is configured to bias towards the discharge channel in response to gravitational force acting on the mobile body when the detector main body is disposed in an initial position. The mobile body is shaped to enable fluid to flow through the fluid flow channel at a predetermined minimum flow rate. The mobile body can be spherically shaped.

In embodiments, the fluid flow channel is configured to receive a drug solution for passage to a patient's body. In embodiments, one or both of the upstream end and the downstream end of the fluid flow channel are configured to engage a medical device. In embodiments, the fluid flow detector includes one or more combined detection and discharge channels positioned between the fluid flow detection channel and the discharge channel.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1:
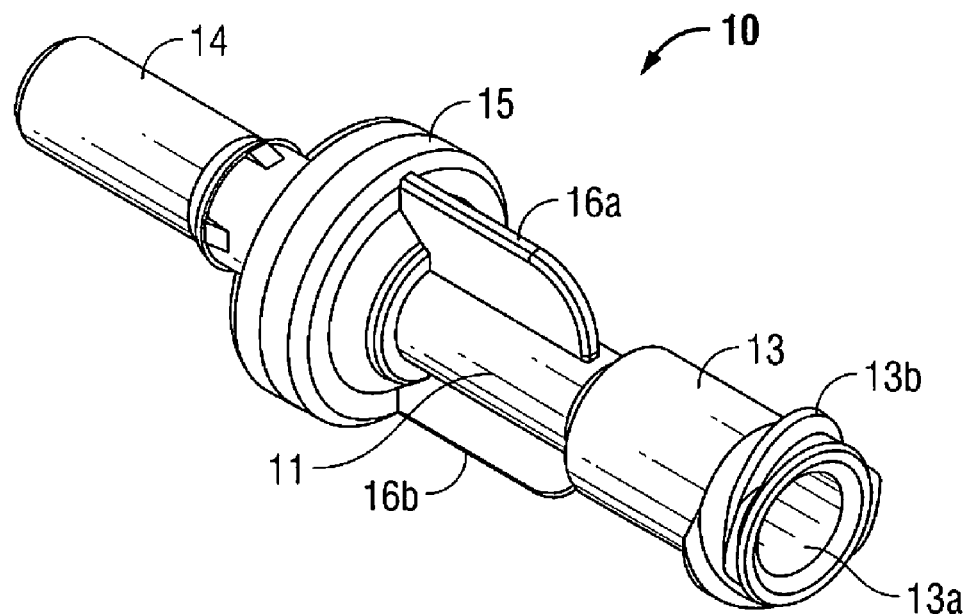
FIG. 1 is an oblique view showing a fluid flow detector according to one embodiment of the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Figure 2:
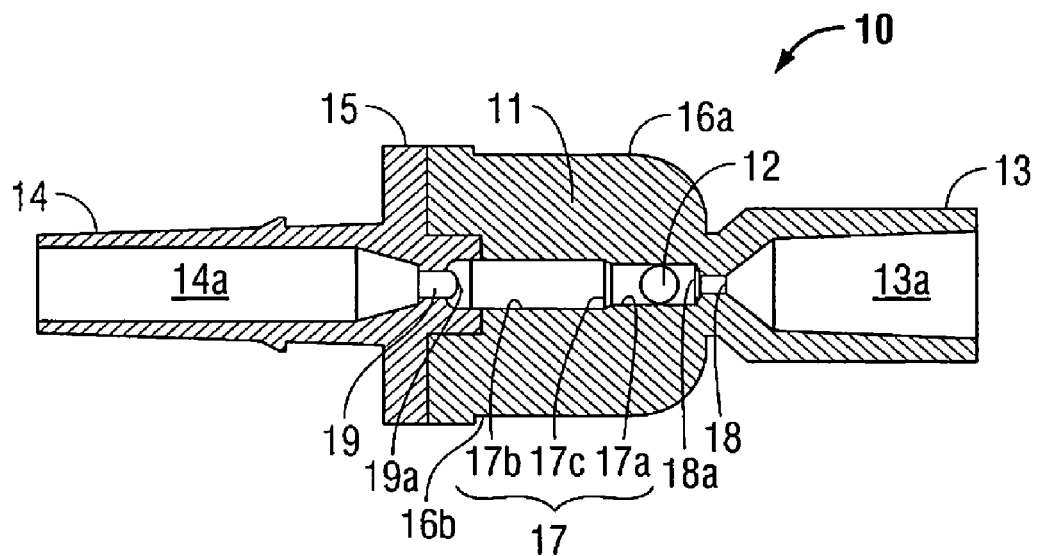
FIG. 2 is a cross-sectional view of the fluid flow detector of FIG. 1.
Figure 4:
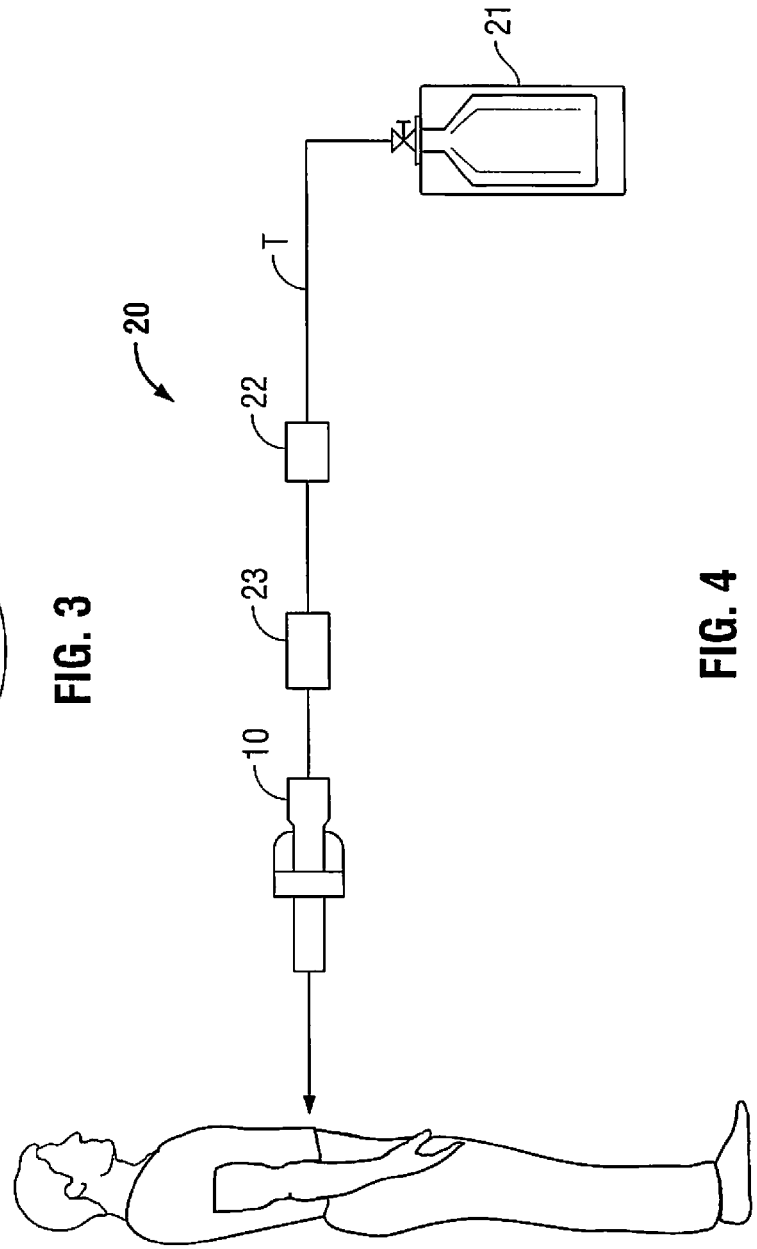
FIG. 4 is a block diagram showing a schematic of a transfusion line set including the fluid flow detector of FIGS. 1-2.

A fluid flow detector according to one embodiment of the present disclosure and a transfusion line provided with the same will be described below in detail with reference to the figures. FIGS. 1 and 2 show a fluid flow detector 10 according to one embodiment of the disclosure. The fluid flow detector 10 is used to detect the flow of a minute amount of a fluid such as a drug solution (referred to hereinbelow as "fluid" and referenced "F" in FIGS. 5B-6) which is flowing inside tubes T (which define the fluid supply channel and are shown in FIG. 4) of a transfusion line set 20. The fluid flow detector 10 comprises a detector main body 11, a mobile spherical body 12 arranged inside the detector main body 11 which acts as the mobile body according to the present disclosure, an inflow pipe 13 provided at the upstream side or rear part of the detector main body 11 (the right-hand side in FIGS. 1 and 2), an outflow pipe 14 provided at the downstream side or front part of the detector main body 11, and grip parts 15, 16a, 16b formed on the periphery of the detector main body 11.

Referring to FIG. 2, the detector main body 11 is cylindrical and defines a fluid flow channel 17 comprising a fluid flow detection channel 17a, a discharge channel 17b, and an intermediate flow channel 17c positioned between the fluid flow detection channel 17a and the discharge channel 17b. An upstream hole 18 which links the fluid flow detection channel 17a in communication with an upstream fluid flow channel 13a formed inside the inflow pipe 13 is formed at the upstream end of the fluid flow detection channel 17a, and a downstream hole 19 which links the discharge channel 17b in communication with a downstream fluid flow channel 14a formed inside the outflow pipe 14 is formed at the downstream end of the discharge channel 17b.

The fluid flow detection channel 17a consists of a hole extending from front to rear with a constant diameter (e.g., 1.6 mm), and it is approximately ⅓ of the length of the fluid flow channel 17 in the front to rear direction (e.g., 3.0-4.0 mm). The discharge channel 17b includes a hole extending from front to rear with a constant diameter (e.g., 2.0 mm), and it is approximately ⅔ of the length of the fluid flow channel 17 in the front to rear direction (e.g., 7.0-8.0 mm). The intermediate flow channel 17c consists of a hole having a tapering inner peripheral surface, in which the diameter at its upstream end is substantially the same as the diameter of the fluid flow detection channel 17a, and the diameter at its downstream end is substantially the same as the diameter of the discharge channel 17b. The length of the fluid flow channel 17 in the front to rear direction can be, for example, set at approximately 10-12 mm.

The upstream hole 18 consists of a hole in which the outer periphery of the face (space) orthogonal to the flow of fluid is elliptical, and the length along the major axis of the ellipse (horizontal direction) is set at e.g., about 1.2 mm, with the length along the minor axis of the ellipse (vertical direction) being set at e.g., about 0.8 mm. A step 18a is formed between the fluid flow detection channel 17a and the upstream hole 18. The downstream hole 19 includes a hole which is larger than the upstream hole 18 in which the outer periphery of the face (space) orthogonal to the flow of fluid is elliptical, and the length along the major axis of the ellipse (horizontal direction) is set at, e.g., about 1.8 mm, with the length along the minor axis of the ellipse (vertical direction) being set at, e.g., about 1.2 mm.

A linking hole 19a which is tapered so as to become steadily narrower from the side of the discharge channel 17b moving towards the side of the downstream hole 19 is formed between the discharge channel 17b and the downstream hole 19. This linking hole 19a has an upstream end formed as a circle having substantially the same diameter as the diameter of the discharge channel 17b, becoming steadily narrower as it approaches the downstream hole 19, and also it becomes an ellipse whereof the major axis in the horizontal direction is longer than the minor axis in the vertical direction. This detector main body 11, and the inflow pipe 13, outflow pipe 14 and grip parts 15, 16a, 16b which will be described later, can be made of polycarbonate, polypropylene, or similar material.

The mobile spherical body 12 is arranged in the fluid flow channel 17 and can be made of polytetrafluoroethylene, which has excellent resistance to drugs. In embodiments, body 12 has a diameter of about 1.5 mm, and a specific gravity of about 2.13-2.22. It is also possible to use polyacetal (specific gravity 1.41-1.42) or polypropylene (specific gravity 0.90-0.91). Consequently, if the direction of flow of the fluid inside the fluid flow channel 17 is made horizontal, and the mobile spherical body 12 is positioned at the upstream side inside the fluid flow detection channel 17a (FIGS. 5C and 6), there is only a small gap between the inner peripheral surface of the fluid flow detection channel 17a and the outer peripheral surface of the mobile spherical body 12. Therefore the mobile spherical body 12 presents resistance to the flow of fluid and moves to the side of the discharge channel 17b with the flow of fluid, even if the fluid flow rate is minute.

Figure 3:
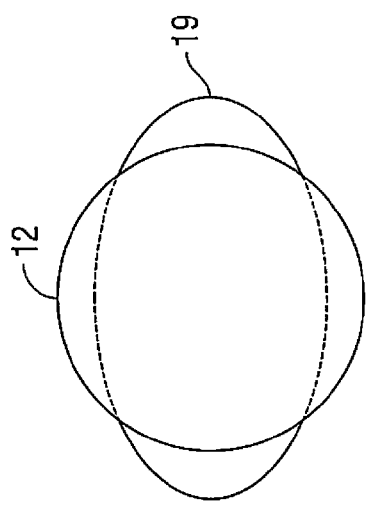
FIG. 3 is a schematic view illustrating the relationship between a downstream hole and a mobile body of the fluid flow detector of FIGS. 1 and 2.
Figure 5A:
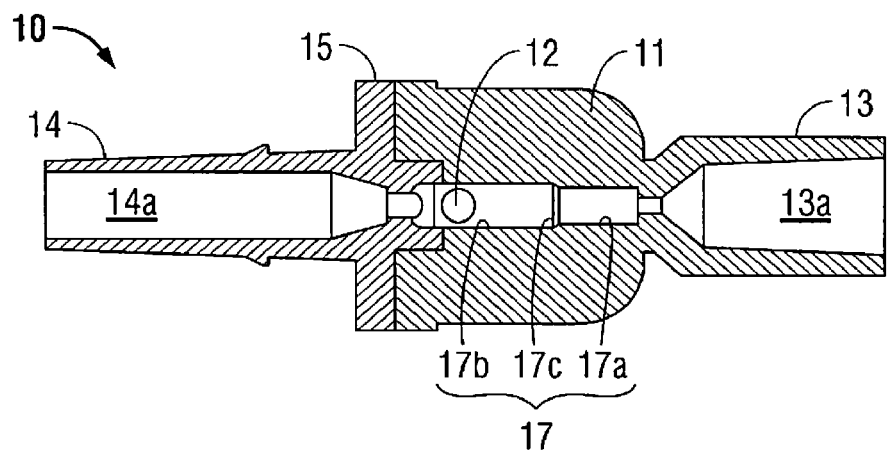
FIG. 5A is a cross-sectional view of the fluid flow detector of FIGS. 1-2 shown in a first condition.
Figure 5B:
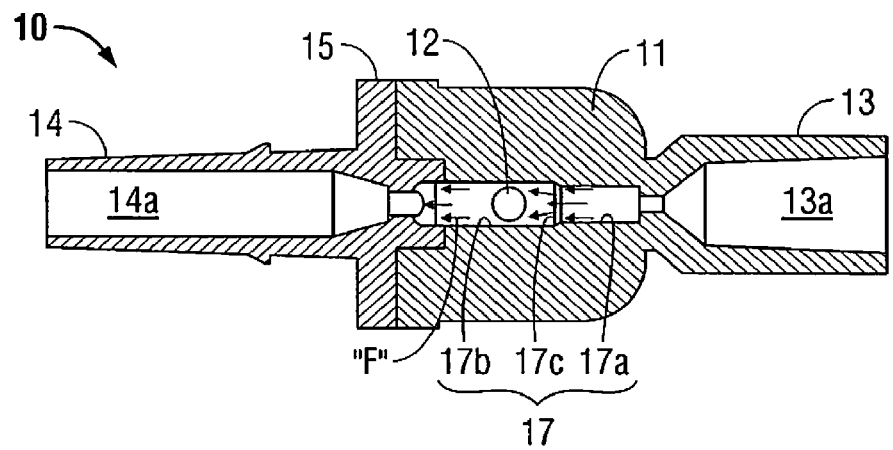
FIG. 5B is a cross-sectional view of the fluid flow detector of FIGS. 1-2 shown in a second condition.
Figure 5C:
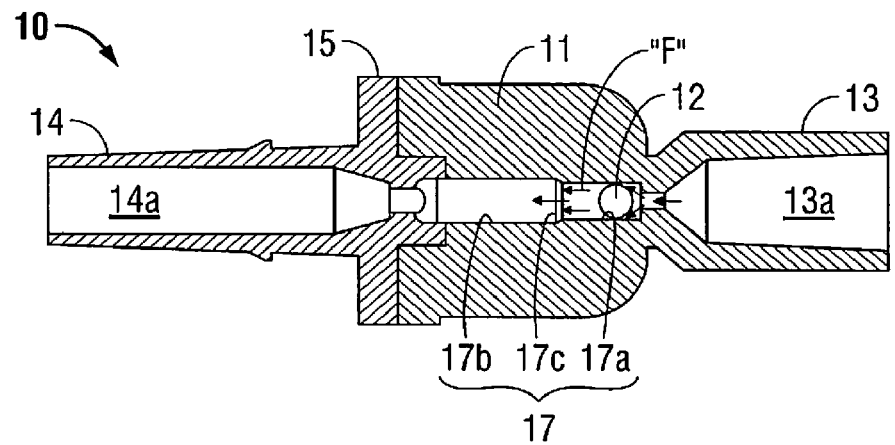
FIG. 5C is a cross-sectional view of the fluid flow detector of FIGS. 1-2 shown in a third condition.
Figure 6:
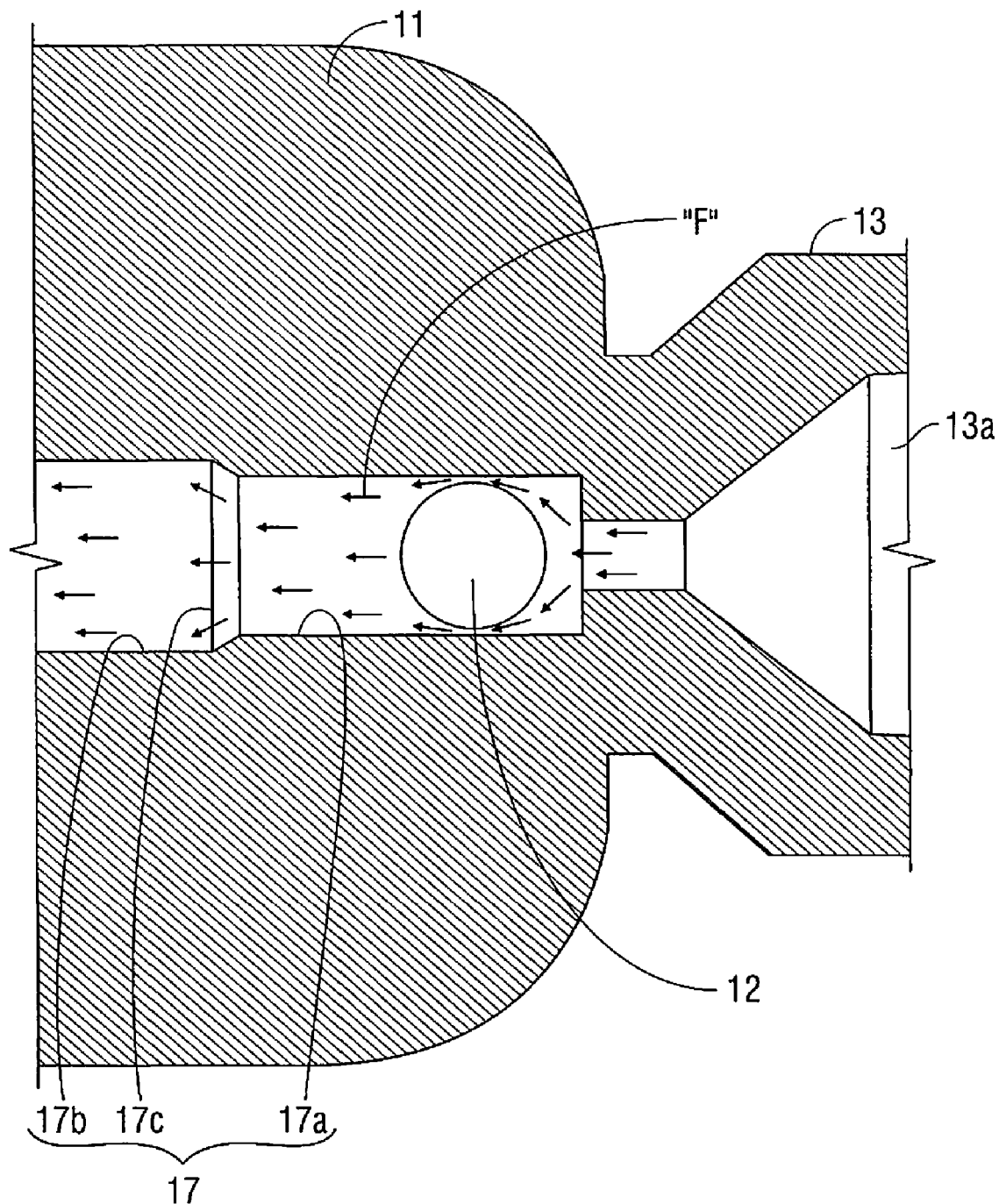
FIG. 6 is an enlarged, cross-sectional view of a portion of the fluid flow detector of FIGS. 1-2 showing a path of fluid flow in a fluid flow detection channel thereof around the mobile body disposed therein when the fluid flow detector is disposed in the third condition as shown in FIG. 5C.

When the mobile spherical body 12 is positioned inside the discharge channel 17b, there is a reasonable size of gap between the inner peripheral surface of the discharge channel 17b and the outer peripheral surface of the mobile spherical body 12, and therefore there is little or no resistance to the flow of fluid due to the mobile spherical body 12 (FIGS. 5A and 5B). Consequently, the mobile spherical body 12 remains static at the lower part of the inner peripheral surface of the discharge channel 17b (FIG. 5A), or moves steadily towards the downstream hole 19 (FIG. 5B), depending on the flow rate of the fluid. In this case, the positional relationship between the mobile spherical body 12 and the downstream hole 19 is as shown in FIG. 3, even if the flow rate of fluid is high and the mobile spherical body 12 has reached the opening of the downstream hole 19.

Consequently, the mobile spherical body 12 cannot pass through the downstream hole 19 and move into the downstream fluid flow channel 14a, and only fluid passes through the downstream hole 19 and flows into the downstream fluid flow channel 14a. Furthermore, in the same way, when the fluid flow detection channel 17a is positioned lower down than the discharge channel 17b so that the mobile spherical body 12 reaches the opening of the upstream hole 18, the positional relationship between the mobile spherical body 12 and the upstream hole 18 is as shown in FIG. 3. Thus, the mobile spherical body 12 cannot pass through the upstream hole 18 and move into the upstream fluid flow channel 13a, and fluid passes through the upstream hole 18 and flows into the fluid flow detection channel 17a.

The inflow pipe 13 includes a female luer in which the diameter of the upstream fluid flow channel 13a formed therein becomes steadily smaller from the opening side moving towards the side of the upstream hole 18, and a thread 13b (omitted from FIG. 2) is formed on the outer periphery of the opening part. A male luer part which is attached to the tip end of a specific tube T from the plurality of tubes T can be engaged at the inflow pipe 13. The outflow pipe 14 includes a male luer in which the diameter of the outer peripheral surface of the front end portion (a portion of approximately ⅓ of the whole length) becomes steadily smaller from the base end side towards the front end side of the outflow pipe 14, and a female luer part attached to the tip end of a specific tube T can be engaged at the outflow pipe 14.

The grip part 15 is provided on the outer periphery of a portion of the detector main body 11 on the outflow pipe 14 side, and can be formed as a disc shape. The downstream hole 19, linking hole 19a, downstream end of the discharge channel 17b and upstream end of the downstream fluid flow channel 14a in the detector main body 11 are positioned inside this grip part 15, and the thickness of the grip part 15 corresponds to these. The grip parts 16a, 16b can be both formed as plate shapes which project outwards from the outer peripheral surface of the detector main body 11. These grip parts 16a, 16b extend in the axial direction of the detector main body 11 with an interval between each other of about 180°, and the front end thereof reaches the rear surface of the grip part 15. The grip part 15 or grip parts 16a, 16b are gripped with the hand when the fluid flow detector 10 is operated.

The fluid flow detector 10 configured in this way is incorporated into the transfusion line set 20 shown in FIG. 4. This transfusion line set 20 configures the transfusion line according to the present disclosure and comprises an infuser 21, a filter 22 and a flow restriction filter 23. The fluid flow detector 10 is arranged downstream of the flow restriction filter 23. Each device of the transfusion line set 20 is then connected by means of specific tubes T. The infuser 21 is provided with an expandable fluid container and an open/close operating part for opening and closing the fluid container, and fluid is housed inside the fluid container. When the outflow port of the fluid container is opened by operation of the open/close operating part, the fluid is pushed out by the force of contraction of the fluid container.

The filter 22 absorbs foreign bodies in the fluid delivered from the infuser 21, removing them from the fluid. The flow rate restriction filter 23 makes the flow rate of the fluid delivered from the infuser 21, via the filter 22, constant and directs fluid to the fluid flow detector 10 on the downstream side. The fluid flow detector 10 allows the fluid to pass through, and is operated when the flow of fluid is to be confirmed, as required. The fluid which has passed through the fluid flow detector 10 is then supplied to the patient's body. That is to say, when the transfusion line set 20 is used, the downstream end of the tube T is connected to a puncture needle (not depicted), such as an indwelling needle, which pierces the patient's body and remains indwelling.

In use, drug solution flows from the infuser 21 into each of the tubes T, and air inside each of the devices which make up the transfusion line set 20 is flushed out, after which the flow of fluid is stopped for a time. In this state, a puncture needle is made to pierce a specific point on the patient's body, and fluid once again flows into the tubes T etc. By means of this, fluid at a set and constant flow rate is supplied to the patient's body from the infuser 21. At this time, the fluid flow detection channel 17a may be positioned higher up than the discharge channel 17b, and the mobile spherical body 12 may be positioned inside the discharge channel 17b. By means of this, it is possible to reliably prevent the mobile spherical body 12 from obstructing the flow of fluid inside the fluid flow detector 10. Then, if necessary, it can be confirmed whether or not the fluid is flowing properly using the fluid flow detector 10.

In this case, the mobile spherical body 12 is first of all moved to the upstream end of the fluid flow detection channel 17a by inclining the fluid flow detector 10 so that the fluid flow detection channel 17a is lower than the discharge channel 17b. Once the mobile spherical body 12 has reached the upstream end of the fluid flow detection channel 17a, the fluid flow detector 10 is placed on a base or the like having a horizontal surface, and the direction of flow of the fluid inside the fluid flow channel 17 is set to the horizontal. When the mobile spherical body 12 is moved inside the fluid flow detection channel 17a towards the discharge channel 17b, it is judged that the fluid is flowing properly. If the mobile spherical body 12 is static, it is judged that the fluid is not flowing, and the necessary steps are taken. If it is judged that the fluid is flowing properly, the fluid flow detection channel 17a may be once again positioned higher up than the discharge channel 17b, and the mobile spherical body 12 may be positioned inside the discharge flow channel 17b.

As described above, with the fluid flow detector 10 according to this mode of embodiment, the fluid flow channel 17 comprising the fluid flow detection channel 17a, discharge channel 17b and intermediate flow channel 17c, is formed inside the detector main body 11, and the mobile spherical body 12 is arranged inside flow channel 17. Then, the diameter of the fluid flow detection channel 17a is set to be slightly greater than the diameter of the mobile spherical body 12, and the diameter of the discharge channel 17b is set to be even greater than the diameter of the fluid flow detection channel 17a. Accordingly, when the mobile spherical body 12 is positioned at the upstream end of the fluid flow detection channel 17a in a state in which the fluid flow channel 17 of the detector main body 11 is horizontally positioned, the mobile spherical body 12 moves from the upstream side towards the downstream side of the fluid flow detection channel 17a when the fluid is flowing properly inside the fluid flow channel 17 from the upstream side towards the downstream side.

By means of this, it is possible to detect that the fluid is flowing inside the fluid flow channel 17. Furthermore, when the mobile spherical body 12 is positioned inside the discharge channel 17b, there is a large gap between the inner peripheral surface of the discharge channel 17b and the outer peripheral surface of the mobile spherical body 12, and therefore there is no obstruction to the flow of fluid. Furthermore, the peripheral edge parts of the upstream hole 18 and downstream hole 19 which are provided at both ends of the fluid flow channel 17 are formed as an ellipse, and therefore it is possible to prevent the mobile spherical body 12 from moving outside of the fluid flow channel 17, and also to prevent the flow of fluid stopping because of the mobile spherical body 12 coming into abutment with the peripheral edge parts of the upstream hole 18 or downstream hole 19. Furthermore, the tapering intermediate flow channel 17c is provided between the fluid flow detection channel 17a and the discharge channel 17b, and therefore it is possible to carry out a smooth operation to move the mobile spherical body 12 from the discharge channel 17b to the fluid flow detection channel 17a.

The fluid flow detector 10 according to the present disclosure is not limited to the mode of embodiment described above, and suitable modifications can be implemented. For example, in the mode of embodiment described above, the diameter of the fluid flow detection channel 17a is set at 1.6 mm, and the diameter of the mobile spherical body 12 is set at 1.5 mm, but both of these diameters may be suitably modified depending on the flow rate of the fluid. If the flow of fluid is no more than 1 ml per hour, for example, the diameter of the fluid flow detection channel 17a and the diameter of the mobile spherical body 12 are set so that the area of the minimum gap between the inner peripheral surface of the fluid flow detection channel 17a and the outer peripheral surface of the mobile spherical body 12 is even smaller.

Furthermore, if the flow of fluid is greater than 1 ml per hour, the diameter of the fluid flow detection channel 17a and the diameter of the mobile spherical body can be set so that the area of the minimum gap between the inner peripheral surface of the fluid flow detection channel 17a and the outer peripheral surface of the mobile spherical body 12 is slightly greater. In addition, in the mode of embodiment described above, the shape of the peripheral edge part of the upstream hole 18 and downstream hole 19 is made elliptical so that fluid passes through without being obstructed by the mobile spherical body 12, but the mobile-spherical body 12 does not pass through. Other shapes may, however, be employed instead of elliptical.

For example, it is possible to allow only fluid to pass through by providing a groove part at the peripheral edge part of circular holes, or similar. Furthermore, it is possible to allow only fluid to pass through by providing the circular holes with a filter. In addition, in the mode of embodiment described above, the mobile body is configured by the mobile spherical body 12, but a columnar body, a body in which the centre axis of two conical bodies has been placed coaxially and the tops of the two conical bodies are linked, or a body in which the centers of two facing discs are linked by a shaft, or similar can also be used instead of the mobile spherical body 12. Furthermore, the mobile body may be moved by forming a face on the upstream side of the mobile body as a recess instead of a convex surface or planar surface, and making the fluid come into contact with the recess. In addition, the diameter of the discharge flow channel 17b may be set so that the downstream side is larger than the upstream side, and the inner peripheral surface of the discharge channel 17b may be tapered. In this case, the intermediate flow channel 17c may be omitted. In addition, the structure and material of the various members making up the fluid flow detector 10, and the specific gravity etc. of the mobile spherical body 12 may be suitably modified within the technical scope of the present disclosure.

Figure 7:
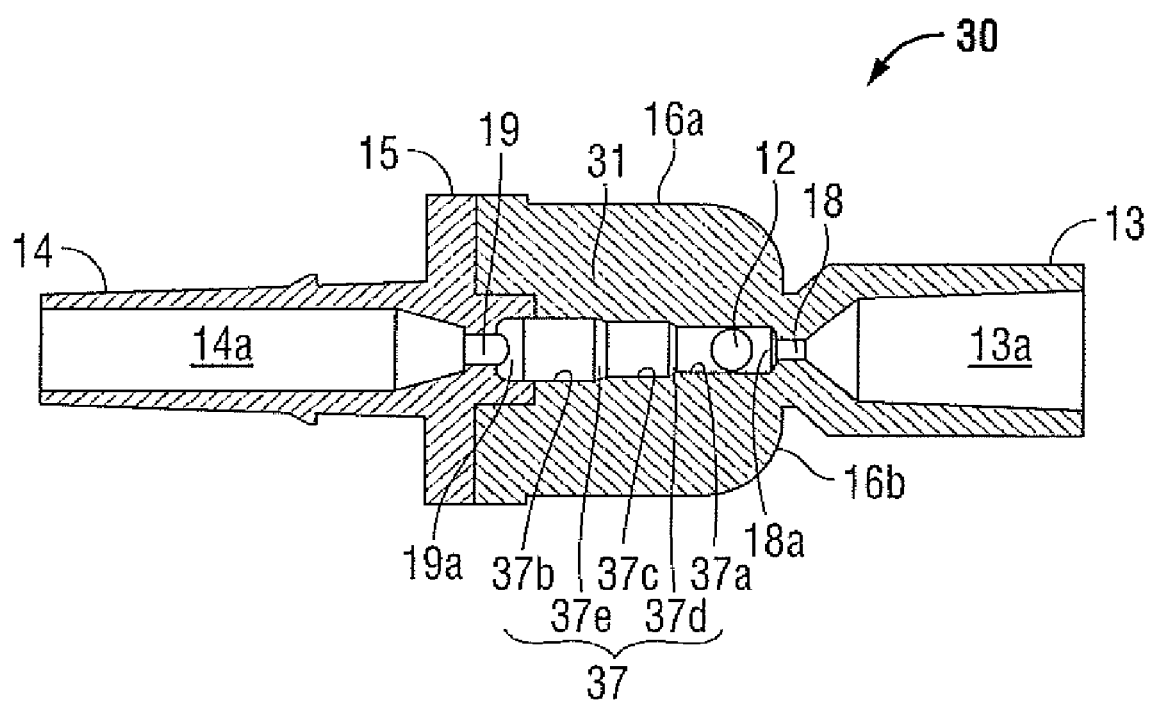
FIG. 7 is a cross-sectional view of another embodiment of a fluid flow detector in accordance with the principles of the present disclosure.

FIG. 7 shows a fluid flow detector 30 according to a second mode of embodiment of the present disclosure. A detector main body 31 of this fluid flow detector 30 has a cylindrical shape (see the portion denoted by the symbol 11 in FIG. 1), and it has formed inside it a fluid flow channel 37 comprising a fluid flow detection channel 37a, a discharge channel 37b, and a combined detection and discharge channel 37c positioned between the fluid flow detection channel 37a and the discharge channel 37b. Furthermore, an intermediate flow channel 37d is formed between the fluid flow detection channel 37a and the combined detection and discharge channel 37c, and an intermediate flow channel 37e is formed between the combined detection and discharge channel 37c and the discharge channel 37b. The length of the fluid flow detection channel 37a is substantially equal to the length of the fluid flow detection channel 17a described above, and the lengths of the discharge channel 37b and the combined detection and discharge channel 37c are substantially the same.

Furthermore, the diameter of the combined detection and discharge channel 37c is set to be constant at, e.g., about 1.8 mm. The intermediate flow channel 37d consists of a hole having a tapering inner peripheral surface, in which the diameter at its upstream end is substantially the same as the diameter of the fluid flow detection channel 37a, and the diameter at its downstream end is substantially the same as the diameter of the combined detection and discharge channel 37c. The intermediate flow channel 37e includes a hole having a tapering inner peripheral surface, in which the diameter at its upstream end is substantially the same as the diameter of the combined detection and discharge channel 37c, and the diameter at its downstream end is substantially the same as the diameter of the discharge channel 37b. The structures of the other components of the fluid flow detector 30 are the same as those of the fluid flow detector 10 according to the first mode of embodiment described above. Components which are the same therefore bear the same reference symbols and they will not be described here.

When the fluid flow detector 30 is used to detect the flow of fluid flowing in the tubes T of the transfusion line set 20, the same operation is carried out as in the mode of embodiment described above. That is to say, the mobile spherical body 12 is moved to the upstream end of the fluid flow detection channel 37a, after which the fluid flow detector 30 is placed horizontally so that the fluid inside the fluid flow channel 37 is made to flow in a horizontal direction. In this case, the tapering intermediate flow channel 37e lies between the discharge channel 37b and the combined detection and discharge channel 37c, and the tapering intermediate flow channel 37d lies between the combined detection and discharge channel 37c and the fluid flow detection channel 37a, and therefore the mobile spherical body 12 can move smoothly from the discharge channel 37b to the fluid flow detection channel 37a. It is then observed whether or not the mobile spherical body 12 moves inside the fluid flow detection channel 37a towards the discharge channel 37b.

If the flow rate of the fluid flowing inside the fluid flow channel 37 is high and the mobile spherical body 12 does not readily move to the upstream end of the fluid flow detection channel 37a, then the fluid flow detector 30 is placed horizontally so that the fluid inside the fluid flow channel 37 is made to flow in a horizontal direction, once the mobile spherical body 12 has moved to the upstream side of the combined detection and discharge channel 37c. By means of this, it can be observed whether or not the mobile spherical body 12 moves inside the combined detection and discharge channel 37c towards the discharge channel 37b, whereby it can be judged whether or not the fluid is flowing properly inside the fluid flow channel 37. If the mobile spherical body 12 is static, it is judged that the fluid is not flowing, and the necessary steps are taken.

With the fluid flow detector 30 according to this mode of embodiment, the combined detection and discharge channel 37c is provided between the fluid flow detection channel 37a and the discharge channel 37b. The diameter of the combined detection and discharge channel 37c is set to be between the size of the diameter of the fluid flow detection channel 37a and the diameter of the discharge channel 37b. Consequently, the combined detection and discharge channel 37c can be used as a discharge channel for the fluid flow detection channel 37a, and it can be used as a fluid flow detection channel for the discharge channel 37b. This means that even if there is a wide range of flow velocities in the fluid flowing in the tubes T of the transfusion line set 20, it is possible to obtain a fluid flow detector which can deal with these flow velocities. The other operational effects of the fluid flow detector 30 are the same as those of the fluid flow detector 10 described above.

Fluid flow detectors according to the present disclosure are not limited to the modes of embodiment described above, and suitable modifications can be implemented. For example, in the modes of embodiment described above, the diameter of the fluid flow detection channels 17a, 37a is set at about 1.6 mm, and the diameter of the mobile spherical body 12 is set at about 1.5 mm, but both of these diameters may be suitably modified depending on the flow rate of the fluid. If the flow of fluid is no more than 1 ml per hour, for example, the diameter of the fluid flow detection channels 17a, 37a and the diameter of the mobile spherical body 12 can be set so that the area of the minimum gap between the inner peripheral surface of the fluid flow detection channels 17a, 37a and the outer peripheral surface of the mobile spherical body 12 is even smaller.

Furthermore, if the flow of fluid is greater than 1 ml per hour, the diameter of the fluid flow detection channels 17a, 37a and the diameter of the mobile spherical body 12 can be set so that the area of the minimum gap between the inner peripheral surface of the fluid flow detection channels 17a, 37a and the outer peripheral surface of the mobile spherical body 12 is slightly greater. In addition, in the modes of embodiment described above, the shape of the peripheral edge of the upstream hole 18 and downstream hole 19 is made elliptical so that fluid passes through without being obstructed by the mobile spherical body 12, but the mobile spherical body 12 does not pass through. Other shapes may, however, be employed instead of elliptical.

For example, it is possible to allow only fluid to pass through by providing a groove part at the peripheral edge of circular holes, or similar. Furthermore, it is possible to allow only fluid to pass through by providing the circular holes with a filter. In addition, in the modes of embodiment described above, the mobile body is configured by the mobile spherical body 12, but a columnar body, a body in which the centre axis of two conical bodies has been placed coaxially and the tops of the two conical bodies are linked, or a body in which the centers of two facing discs are linked by a shaft, or similar structure can also be used instead of the mobile spherical body 12. Furthermore, the mobile body may be moved by forming a face on the upstream side of the mobile body as a recess instead of a convex surface or plane surface, and making the fluid come into contact with the recess.

In addition, the diameter of the discharge flow channel 17b of the fluid flow detector 10 may be set so that the downstream side is larger than the upstream side, and the inner peripheral surface of the discharge channel 17b may be tapered. In this case, the intermediate flow channel 17c may be omitted. Furthermore, a number of combined detection and discharge channels having different diameters may be provided instead of the combined detection and discharge channel 37c of the fluid flow detector 30. In addition, the structure and material of the various members making up the fluid flow detectors 10, 30, and the specific gravity of the mobile spherical body 12 etc. may be suitably modified within the technical scope of the present disclosure.

Although specific features of the disclosure are shown in some drawings and not in others, this for convenience only as each feature may be combined with any or all of the other features in accordance with the invention. Other embodiments will occur to those skilled in the art and are within the following claims.

What is claimed is:

1. A fluid flow detector for detecting the flow of a fluid in a transfusion line, comprising:
    a detector main body defining a fluid flow channel having a circular cross section and comprising, an upstream hole formed at an upstream end of the detector main body, a downstream hole formed at a downstream end of the detector main body, a fluid flow detection channel positioned adjacent the upstream hole, a discharge channel positioned adjacent the downstream hole, and at least one combined detection and discharge channel positioned between the fluid flow detection channel and the discharge channel; and
    a mobile body positioned within the fluid flow channel and dimensioned to be movable along the fluid flow channel in response to the flow of a fluid inside the fluid flow channel, and in which an outer peripheral edge part of a face of the fluid flow channel which is orthogonal to the direction of movement is formed to be circular;
    wherein the diameter of the fluid flow detection channel is smaller than the diameter of the discharge channel, and the maximum diameter of the outer peripheral edge part of the face of the fluid flow channel orthogonal to the direction of movement of the mobile body is set to be smaller than the diameter of the fluid flow detection channel, and the upstream hole and the downstream hole are formed with a size and shape such that fluid can flow around the mobile body through the upstream and downstream holes;
    wherein an intermediate flow channel is positioned between the at least one combined detection and discharge channel and at least one of the fluid flow detection channel and the discharge channel, the intermediate flow channel having a diameter that continuously increases from the fluid flow detection channel towards the discharge channel; and
    wherein the intermediate flow channel has a length in a longitudinal direction that is smaller than the diameter of the outer peripheral edge part of the mobile body.

2. The fluid flow detector according to claim 1, in which the mobile body consists of a spherical body.

3. The fluid flow detector according to claim 1, wherein the fluid flow channel from between the upstream hole and the downstream hole consists of a shape in which the peripheral edge part of the upstream hole and downstream hole orthogonal to the flow of fluid is elliptical.

4. The fluid flow detector according to claim 1, in which an inflow pipe comprising a female luer which links in communication with the fluid flow channel is joined to the upstream hole of the detector main body, and an outflow pipe comprising a male luer which links in communication with the fluid flow channel is joined to the downstream hole of the detector main body.

5. The fluid flow detector according to claim 1, wherein the fluid flow detector is incorporated into a transfusion line that includes a fluid supply part and a fluid supply channel through which passes a fluid supplied from the fluid supply part, and the fluid flow detector is arranged in the fluid supply channel.

6. A fluid flow detector, comprising:
a detector main body defining a fluid flow channel having an upstream end and an downstream end, the fluid flow channel defining a fluid flow detection channel disposed on the upstream end, a discharge channel disposed on the downstream end, at least one combined detection and discharge channel positioned between the fluid flow detection channel and the discharge channel; and
a mobile body movably disposed within the fluid flow channel between the fluid flow detection and discharge channels, wherein the discharge channel has a diameter larger than the fluid flow detection channel, and wherein the mobile body is configured to be selectively positioned within the fluid flow detection channel to provide indicia of fluid flow within the fluid flow detection channel;
wherein an intermediate flow channel is positioned between the at least one combined detection and discharge channel and at least one of the fluid flow detection channel and the discharge channel, the intermediate flow channel having a diameter that continuously increases from the fluid flow detection channel towards the discharge channel; and
wherein the intermediate flow channel has a length in a longitudinal direction that is smaller than the diameter of the outer peripheral edge part of the mobile body.

7. The fluid flow detector according to claim 6, wherein the mobile body is positioned to move towards the discharge channel in response to gravitational force acting on the mobile body when the detector main body is disposed in an initial position.

8. The fluid flow detector according to claim 6, wherein the diameter of the fluid flow detection channel is slightly larger than the diameter of the mobile body so that fluid may flow past the mobile body within the fluid flow detection channel.

9. The fluid flow detector according to claim 6, wherein the mobile body is shaped and dimensioned to enable fluid to flow through the fluid flow channel at a predetermined minimum flow rate.

10. The fluid flow detector according to claim 6, wherein the mobile body is spherically shaped.

11. The fluid flow detector according to claim 6, wherein the fluid flow channel is dimensioned to accommodate a predetermined minimum flow rate of between about 0.1 ml/hr and about 20 ml/hr.

12. The fluid flow detector according to claim 6, wherein at least one of the fluid flow detection and discharge channels of the fluid flow channel is configured to be visually perceptible to a user.

13. The fluid flow detector according to claim 6, wherein the fluid flow channel is configured to receive a drug solution for passage to a patient's body.

14. The fluid flow detector according to claim 6, wherein at least one of the upstream end and the downstream end of the fluid flow channel is configured to engage a medical device.

* * * * *